(12) United States Patent
Swanson et al.

(10) Patent No.: US 10,231,830 B2
(45) Date of Patent: *Mar. 19, 2019

(54) KIDNEY CAPSULE LEAFLET MATERIAL

(71) Applicant: Boston Scientific SciMed, Inc., Maple Grove, MN (US)

(72) Inventors: Lynne E. Swanson, Edina, MN (US); Crystal Marie Anderson-Cunanan, San Jose, CA (US); Katherine Cora Fazackerley, San Mateo, CA (US); Philip D. Crompton, San Mateo, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 18 days.

This patent is subject to a terminal disclaimer.

(21) Appl. No.: 15/340,242

(22) Filed: Nov. 1, 2016

(65) Prior Publication Data

US 2017/0128201 A1 May 11, 2017

Related U.S. Application Data

(60) Provisional application No. 62/253,225, filed on Nov. 10, 2015.

(51) Int. Cl.
*A61F 2/24* (2006.01)
*A61L 27/36* (2006.01)

(52) U.S. Cl.
CPC .......... *A61F 2/2415* (2013.01); *A61F 2/2412* (2013.01); *A61F 2/2418* (2013.01);
(Continued)

(58) Field of Classification Search
CPC ........................................................ A61F 2/24
See application file for complete search history.

(56) References Cited

U.S. PATENT DOCUMENTS

| 6,409,759 B1 | 6/2002 | Peredo |
| 2002/0094573 A1 | 7/2002 | Bell et al. |

(Continued)

FOREIGN PATENT DOCUMENTS

| WO | 9825549 | 6/1998 |
| WO | 2017062198 | 4/2017 |

(Continued)

OTHER PUBLICATIONS

Billiar, Kristen L. et al., "Biaxial Mechanical Properties of the Native and glutaraldehyde-Treated Aortic Valve Cusp: Part II—A Structural Constitutive Model," Journal of Biomechanical Engineering (2000) vol. 122, pp. 327-335.

(Continued)

*Primary Examiner* — Jacqueline Woznicki
(74) *Attorney, Agent, or Firm* — Pauly, DeVries Smith & Deffner LLC

(57) ABSTRACT

A prosthetic heart valve provided herein can include a kidney capsule tissue leaflet. In some cases, a prosthetic heart valve can include a plurality of leaflets secured together and retained within the expandable tubular member. The kidney capsule tissue can be obtained from a farm animal, such as a cow, pig, horse, goat, or sheep. In some cases, the kidney capsule tissue can be tensioned (e.g., bi-axially tensioned) and/or chemically cross-linked.

14 Claims, 6 Drawing Sheets

(52) U.S. Cl.
CPC ............. *A61L 27/3604* (2013.01); *A61F 2/24* (2013.01); *A61F 2210/0076* (2013.01); *A61L 2430/20* (2013.01)

(56) References Cited

U.S. PATENT DOCUMENTS

| | | | |
|---|---|---|---|
| 2002/0103542 | A1 | 8/2002 | Bilbo et al. |
| 2003/0229394 | A1 | 12/2003 | Ogle et al. |
| 2004/0078090 | A1 | 4/2004 | Binette et al. |
| 2005/0143809 | A1 | 6/2005 | Salahieh et al. |
| 2005/0222661 | A1 | 10/2005 | Case et al. |
| 2006/0159722 | A1* | 7/2006 | Braithwaite ............ A61L 27/24 424/427 |
| 2006/0253188 | A1 | 11/2006 | Case et al. |
| 2007/0037283 | A1* | 2/2007 | Patel ................... A61L 26/0033 435/380 |
| 2007/0162103 | A1 | 7/2007 | Case et al. |
| 2007/0254005 | A1 | 11/2007 | Pathak et al. |
| 2009/0138078 | A1 | 5/2009 | Paul, Jr. et al. |
| 2009/0187241 | A1* | 7/2009 | Melsheimer .......... A61F 2/2418 623/2.36 |
| 2009/0216338 | A1 | 8/2009 | Gingras et al. |
| 2014/0277416 | A1 | 9/2014 | Matheny et al. |
| 2016/0296323 | A1 | 10/2016 | Wulfman et al. |
| 2017/0100237 | A1 | 4/2017 | Anderson-Cunanan et al. |
| 2017/0100238 | A1 | 4/2017 | Anderson-Cunanan et al. |

FOREIGN PATENT DOCUMENTS

| | | |
|---|---|---|
| WO | 2017062199 | 4/2017 |
| WO | 2017083183 | 5/2017 |

OTHER PUBLICATIONS

"International Search Report and Written Opinion," for PCT Application PCT/US2016/053680 dated Dec. 16, 2016 (12 pages).
"International Search Report and Written Opinion," for PCT Application PCT/US2016/053682 dated Jan. 3, 2017 (13 pages).
"International Search Report and Written Opinion," for PCT Application PCT/US2016/060449 dated Feb. 24, 2017 (12 pages).
Kelm, J. M. et al., "A Novel Concept for Scaffold-Free Vessel Tissue Engineering: Self-Assembly of Microtissue Building Blocks," Journal of Biotechnology, 148 (2010): pp. 46-55.
"Non-Final Office Action," for U.S. Appl. No. 15/272,747 dated Oct. 19, 2017 (17 pages).
"Non-Final Office Action," for U.S. Appl. No. 15/272,772 dated Mar. 2, 2018 (17 pages).
"Response to Non-Final Office Action," for U.S. Appl. No. 15/272,747, dated Oct. 19, 2017 and filed with the USPTO Dec. 20, 2017 (9 pages).
Cardinal, Kristen O. et al., "Tissue-Engineered Vascular Grafts as In Vitro Blood Vessel mimics for the Evaluation of Endothelialization of Intravascular Devices," Tissue Eng. 12, 3431-3438, 2006 (8 pages).
Gauvin, R. et al., "Dynamic Mechanical Stimulations Include Anisotropy and Improve the Tensile Properties of Engineered Tissues Produced Without Exogenous Scaffolding," Acta. Biomater. 7, 3294-3301, 2011 (8 pages).
Kalejs, et al., "St. Jude Epic Heart Valve Bioprostheses Versus Native Human and Porcine Aortic Valves—Comparison of Mechanical Properties," Interactive Cardiovascular and Thoracic Surgery 8 (2009) 553-557.
Kelm, J. M. et al., "Scaffold-Free Cell Delivery for Use in Regenerative Medicine," Adv. Drug Deliv. Rev. 62, 753-764, 2010 (12 pages).
L'Heureux, N. et al., "A Completely Biological Tissue-Engineered Human Blood Vessel," FASEB J. 12, 47-56, 1998 (10 pages).
Milleret, Vincent et al., "Tuning Electrospinning Parameters for Production of 3D-Fiber-Fleeces with Increased Porosity for Soft Tissue Engineering Applications," Eur. Cell. Mater. 21, 286-303, 2011 (18 pages).
Schellenberg, Anne et al., "3D Non-Woven Polyvinylidene Fluoride Scaffolds: Fibre Cross Section and Texturizing Patterns Have Impact on Growth of Mesenchymal Stromal Cells," PLOS ONE 9(4) e94353, 2014 (9 pages).
"Final Office Action," for U.S. Appl. No. 15/272,747 dated Apr. 25, 2018 (12 pages).
"Final Office Action," for U.S. Appl. No. 15/272,772 dated Jun. 5, 2018 (10 pages).
"International Preliminary Report on Patentability," for PCT Application No. PCT/US2016/053680 dated Apr. 19, 2018 (8 pages).
"International Preliminary Report on Patentability," for PCT Application No. PCT/US2016/053682 dated Apr. 19, 2018 (8 pages).
"International Preliminary Report on Patentability," for PCT Application No. PCT/US2016/060449 dated May 24, 2018 (8 pages).
"Response to Final Office Action," for U.S. Appl. No. 15/272,747 dated Apr. 25, 2018 and filed with the USPTO Jun. 18, 2018 (10 pages).

* cited by examiner

KIDNEY CAPSULE LEAFLET MATERIAL

This application claims the benefit of U.S. Provisional Application No. 62/253,225, filed Nov. 10, 2015, the contents of which are herein incorporated by reference.

FIELD

This document provides leaflets made out of Kidney Capsule Material.

BACKGROUND

Heart valve surgery can be used to repair or replace diseased heart valves. For example, heart valve replacement may be indicated when there is a narrowing of the native heart valve, commonly referred to as stenosis, or when the native valve leaks or regurgitates. The repair or replacement of diseased heart valves can include, for example, the introduction of a prosthetic heart valve that includes biological tissue heterologous to the patient (e.g., a heterograft or xenograft). A common biological tissue used to make prosthetic heart valves is pericardial tissue, typically bovine or porcine.

SUMMARY

Prosthetic heart valves provided herein use kidney capsule tissue as the leaflet material. The kidney capsule, also known as the renal capsule, is a tough fibrous layer surrounding the renal cortex of the kidney and covered in a thick layer of perinephric adipose tissue. It provides some protection from trauma and damage. As used herein, the term "kidney capsule" does not include the renal cortex or the perinephric adipose tissue.

In Example 1, a prosthetic heart valve can include a plurality of leaflets secured together and retained within the expandable tubular member, where each leaflet includes cross-linked kidney capsule tissue.

In Example 2, a prosthetic heart valve of Example 1, where the small intestine submucosa tissue includes multiple layers of kidney capsule tissue.

In Example 3, a prosthetic heart valve of Example 1 or Example 2, wherein the leaflet has a total thickness of between 50 microns and 0.33 mm.

In Example 5, a prosthetic heart valve of one of Examples 1-4, where the kidney capsule tissue has a moisture content of between 73% and 94%.

In Example 6, a prosthetic heart valve of one of Examples 1-5, where the kidney capsule tissue has an ultimate tensile strength of between 3.6 MPa and 8.0 MPa.

In Example 7, a prosthetic heart valve of one of Examples 1-6, where the kidney capsule tissue has a modulus of between 20 and 40.

In Example 8, a prosthetic heart valve of one of Examples 1-7, where the kidney capsule tissue has a percent elongation at 1 MPa of between 5% and 10%.

In Example 9, a prosthetic heart valve of one of Examples 1-8, where the kidney capsule tissue has an elongation to break at between 50% and 75%.

In Example 10, a prosthetic heart valve of one of Examples 1-9, where the tissue bi-axially oriented.

In Example 11, a prosthetic heart valve of one of Examples 1-10, where tissue is cross-linked by submerging the kidney capsule tissue in a solution of between 0.1 and 1.5 wt % glutaraldehyde for at least 10 minutes.

In Example 12, a prosthetic heart valve of one of Examples 1-10, where the tissue is cross-linked by submerging the kidney capsule tissue in a solution of between 0.5 and 1.0 wt % glutaraldehyde for at least 30 minutes.

In Example 13, a prosthetic heart valve of one of Examples 1-10, where the tissue is cross-linked by submerging the kidney capsule tissue in a solution of between 0.5 and 0.7 wt % glutaraldehyde for at least 2 hours.

In Example 14, a prosthetic heart valve of one of Examples 1-13, where the leaflets consist of the cross-linked kidney capsule tissue.

In Example 15, a method of forming a kidney capsule leaflet includes: (a) obtaining kidney capsule; (b) cutting and stacking multiple layers of the kidney capsule into a substantially planar patch of kidney capsule tissue having a thickness of at least 50 microns; (c) contacting the kidney capsule tissue with a chemical cross-linker for at least 10 minutes to cross-link the patch; and (e) cutting out a leaflet from the patch, the leaflet comprising a body portion and two sleeve portions.

In Example 16, the method of Example 15 where the chemical cross-linker is glutaraldehyde.

In Example 17, the method of Example 16 where the kidney capsule tissue is submerged in a solution comprises between 0.1 and 1.5 wt % glutaradehyde to cross-link the kidney capsule.

In Example 18, the method of Example 16 where the tissue is cross-linked by submerging the kidney capsule tissue in a solution of between 0.5 and 1.0 wt % glutaraldehyde for at least 30 minutes.

In Example 19, the method of Example 16 where the tissue is cross-linked by submerging the kidney capsule tissue in a solution of between 0.5 and 0.7 wt % glutaraldehyde for at least 2 hours.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1A:
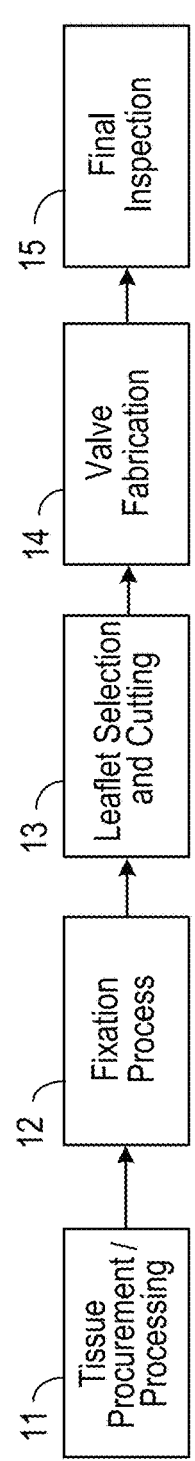
FIG. 1A is flow chart depicting an exemplary method for producing a heart valve using kidney capsule tissues.

Prosthetic heart valves provided herein include cross-linked kidney capsule tissue leaflets. Prosthetic heart valves have typically used bovine or porcine pericardium tissue leaflets, but cross-linked kidney capsule tissue can provide a thinner wall thickness while providing a sufficient ultimate tensile strength and other mechanical properties.

Table I showcases the tensile and thickness properties of two different types of tissue: Porcine kidney capsule and bovine pericardium. Both types of tissue are fixed, or chemically crosslinked, in glutaraldehyde. Fixation bestows unique material properties to tissue subjected to the treatment. By looking at the average values for select outputs, conclusions may be drawn about the differences between the two types of tissue. On average, fixed kidney capsule (FKP) possesses thickness characteristics that are 13% of fixed bovine pericaridum (FBP). Thinner tissue is potentially useful for reducing the profile of implantable devices. On average, FKP possesses an ultimate tensile strength (UTS) that is 39% of FBP. UTS refers to the amount of stress required to fracture a material. On average, FKP possesses a modulus of elasticity that is 33% of FBP.

Modulus of elasticity refers to a material's resistance to being deformed non-permanently (elasticity). Colloquially, this means that FPK is "stretchier" than FBP. On average, FKP possess a strain value at 1 MPa that is 99% of FBP. Strain refers to the amount of deformation that occurs compared to its original size, represented as a percentage. FPK and FBP are functionally identical with regards to this output.

TABLE I

| Type | Dogbone ID | Thickness (in) | Max Load (N) | UTS (MPa) | Modulus of Elasticity (MPa) | Modulus (Tangent 0.5 MPa) | Modulus (Tangent 1 MPa) | Strain @ 500 kPa (%) | Strain @ 1 MPa (%) | Strain @ Failure (%) |
|---|---|---|---|---|---|---|---|---|---|---|
| Fixed Porcine Kidney Capsule | Porcine Kidney Capsule-1 | 0.0023 | 0.964 | 3.7 | 59.516 | 82.126 | 29.446 | 5.66 | 7.49 | 69.48 |
| | Porcine Kidney Capsule-2 | 0.0013 | 1.158 | 7.92 | 23.716 | 33.446 | 32.3657 | 6.42 | 8.2 | 60.88 |
| | Porcine Kidney Capsule-3 | 0.0017 | 1.156 | 5.85 | 16.226 | 15.647 | 21.3161 | 3.55 | 6.29 | 74.95 |
| | Porcine Kidney Capsule-4 | 0.0015 | 0.988 | 5.84 | 28.912 | 6.007 | 37.1944 | 3.12 | 5.61 | 54.92 |
| Fixed Bovine Pericaridum | Bovine Pericaridum-1 | 0.0138 | 19.7 | 12.5 | 95.416 | 33.899 | 57.0837 | 3.14 | 4.24 | 28.83 |
| | Bovine Pericaridum-2 | 0.0144 | 4.931 | 3 | 30.737 | 21.928 | 32.1087 | 4.76 | 6.57 | 64.46 |
| | Bovine Pericaridum-3 | 0.014 | 22.63 | 14.2 | 72.248 | 22.634 | 44.0857 | 7.79 | 9.32 | 33.03 |
| | Bovine Pericaridum-4 | 0.014 | 25.87 | 16.2 | 103.124 | 29.066 | 44.5154 | 3.12 | 4.51 | 24.35 |
| | Bovine Pericaridum-5 | 0.0128 | 4.411 | 3.02 | 26.736 | 18.084 | 27.0361 | 4.14 | 6.37 | 59.83 |
| | Bovine Pericaridum-6 | 0.0116 | 20.78 | 15.6 | 104.035 | 15.575 | 30.5403 | 9.75 | 11.87 | 31.07 |
| | Bovine Pericaridum-7 | 0.0133 | 38.7 | 25.5 | 116.803 | 19.787 | 39.8028 | 7.97 | 9.84 | 41.59 |
| | Bovine Pericaridum-8 | 0.0132 | 28.24 | 18.6 | 109.585 | 28.961 | 46.0128 | 3.62 | 4.98 | 28.46 |
| | Bovine Pericaridum-9 | 0.0154 | 32.35 | 18.4 | 112.07 | 18.001 | 37.6225 | 7.54 | 9.38 | 29.61 |
| | Bovine Pericaridum-10 | 0.0132 | 38.73 | 25.7 | 189.442 | 29.785 | 61.4075 | 3.85 | 4.95 | 27.43 |
| | Bovine Pericaridum-11 | 0.0139 | 13.56 | 8.55 | 61.959 | 23.659 | 42.8677 | 5.45 | 6.99 | 29.02 |
| | Bovine Pericaridum-12 | 0.0131 | 28.92 | 19.3 | 124.216 | 18.671 | 39.8615 | 7.35 | 9.17 | 38.72 |
| | Bovine Pericaridum-13 | 0.0108 | 7.25 | 5.9 | 42.383 | 20.269 | 33.2651 | 4.29 | 6.17 | 42.28 |
| | Bovine Pericaridum-14 | 0.0115 | 28.04 | 21.3 | 132.206 | 17.317 | 41.7616 | 6.46 | 8.29 | 28.65 |
| | Bovine Pericaridum-15 | 0.0145 | 12.72 | 7.66 | 70.699 | 27.625 | 43.2509 | 4.5 | 5.89 | 32.95 |
| | Bovine Pericaridum-16 | 0.0135 | 29.48 | 19.1 | 115.602 | 29.073 | 43.821 | 3.33 | 4.69 | 29.45 |
| | Bovine Pericaridum-17 | 0.0154 | 20.55 | 11.7 | 85.408 | 17.288 | 36.2032 | 7.9 | 9.87 | 34.9 |
| | Bovine Pericaridum-18 | 0.0137 | 17.86 | 11.4 | 91.026 | 28.998 | 43.7671 | 3.79 | 5.23 | 27.14 |
| | Bovine Pericaridum-19 | 0.0112 | 18.63 | 14.5 | 92.77 | 18.312 | 35.1025 | 7.75 | 9.74 | 31.62 |

TABLE I-continued

| Type | Dogbone ID | Thickness (in) | Max Load (N) | UTS (MPa) | Modulus of Elasticity (MPa) | Modulus (Tangent 0.5 MPa) | Modulus (Tangent 1 MPa) | Strain @ 500 kPa (%) | Strain @ 1 MPa (%) | Strain @ Failure (%) |
|---|---|---|---|---|---|---|---|---|---|---|
| | Bovine Pericaridum-20 | 0.0105 | 27.07 | 22.5 | 126.495 | 21.288 | 28.6814 | 5.51 | 7.26 | 35.01 |
| | Bovine Pericaridum-21 | 0.012 | 24.14 | 17.6 | 103.911 | 23.268 | 43.5072 | 6.37 | 7.9 | 43.87 |
| | Bovine Pericaridum-22 | 0.0105 | 25.11 | 20.9 | 126.773 | 33.592 | 55.0018 | 2.96 | 4.05 | 28.55 |
| | Bovine Pericaridum-23 | 0.0162 | 30.08 | 16.3 | 100.629 | 23.058 | 43.5982 | 7.2 | 8.82 | 28.75 |
| | Bovine Pericaridum-24 | 0.0165 | 28.81 | 15.3 | 95.206 | 31.219 | 45.2001 | 2.33 | 3.65 | 33.2 |
| | Bovine Pericaridum-25 | 0.0098 | 9.93 | 8.91 | 78.558 | 37.466 | 56.1373 | 2.69 | 3.74 | 35.83 |

Figure 6:
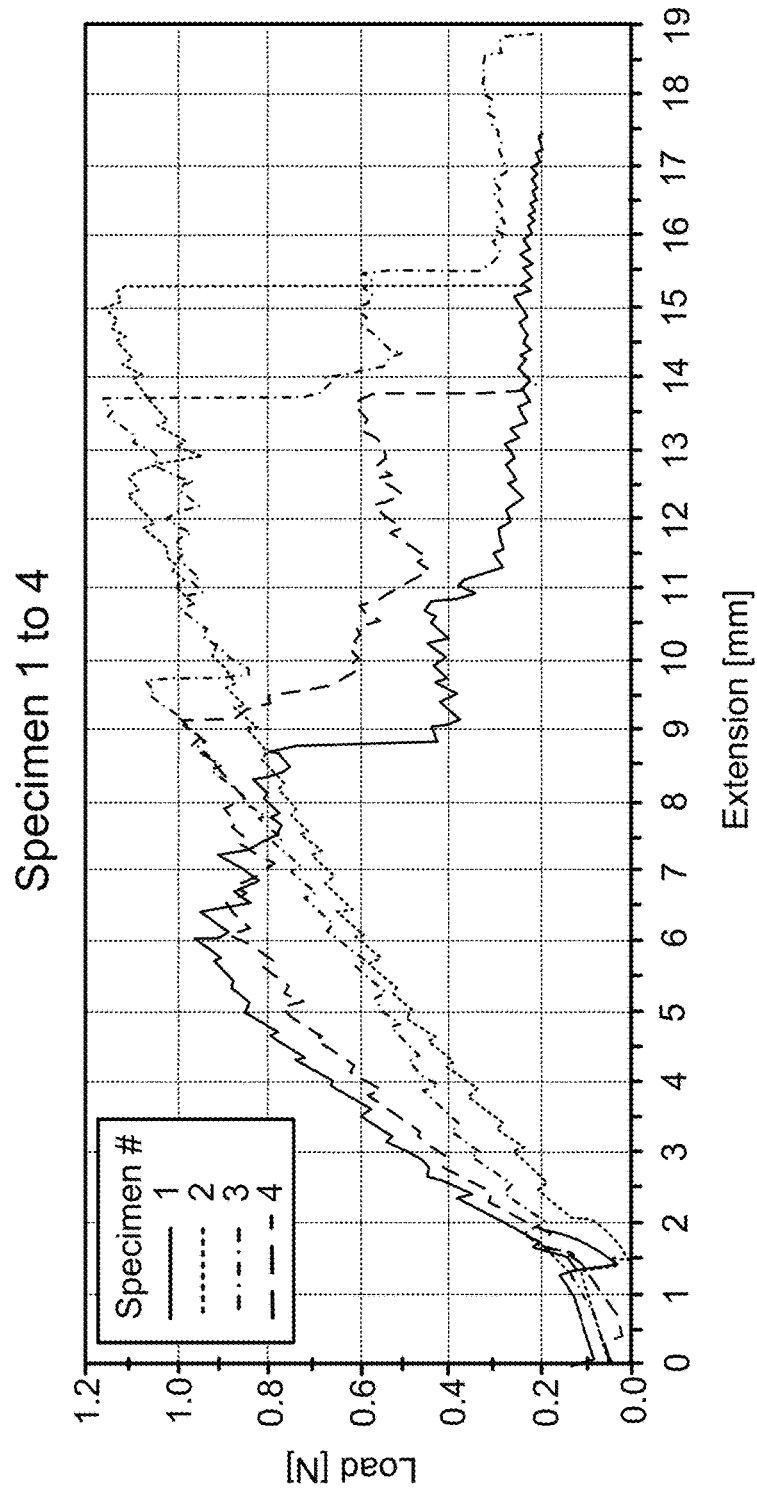
FIG. 6 depicts the load to extension curve for samples of cross-linked porcine kidney capsule tissue.

The samples of porcine kidney capsule tissue in Table 1 are for a single sheet of tissue. In some cases, a leaflet provided herein can include one or more layers of cross-linked kidney capsule tissue. For example, a leaflet can include a laminate containing 2, 3, 4, or 5 or more layers of cross-linked kidney capsule tissue. In some cases, a leaflet included herein can have a total thickness of between 50 microns and 0.33 mm, including one or more layers of cross-linked kidney capsule tissue each having a thickness of between 25 and 75 microns. The samples of porcine kidney capsule tissue samples tested had between 73% and 94% moisture content. Unexpectedly, cross-linked porcine kidney capsule tissue shown in Table I has an average of 86% water content, 0.0017" thick (about 43 microns) has an Ultimate tensile strength of 5.8 MPa. Because the water content of the cross-linked kidney capsule tissue is high compared to bovine pericardium, the kidney capsule tissue can allow for water to be squeezed out to reduce the tissue profile. Additionally, water is a plasticizer, so this could enable the kidney capsule to be more elastic. FIG. 6 depicts the load to extension curve for samples of cross-linked porcine kidney capsule tissue.

In some cases, the cross-liked kidney capsule tissue can be biaxially oriented. In some cases, the kidney capsule tissue can be biaxially tensioned during cross-linking in order to impart the biaxial orientation. In some cases, a sheet of kidney capsule tissue can have a thickness of between 25 microns and 75 microns. In some cases, a leaflet can include one or more layers of kidney capsule tissue to have a total thickness of between 50 microns and 0.33 mm. In some cases, the kidney capsule tissue is bi-axially tensioned by applying a stress load of at least 0.1 N to stretch the kidney capsule tissue along two intersecting axes. In some cases, the kidney capsule tissue is bi-axially tensioned by applying a stress load of between 0.1 N and 2 N to stretch the kidney capsule tissue along two intersecting axes. In some cases, the kidney capsule tissue is bi-axially tensioned by applying a stress load of between 0.5 N and 1 N to stretch the kidney capsule tissue along two intersecting axes. The kidney capsule tissue can be chemically cross-linked while under tension to prevent recoil of the kidney capsule tissue after the tension is released.

Figure 3:
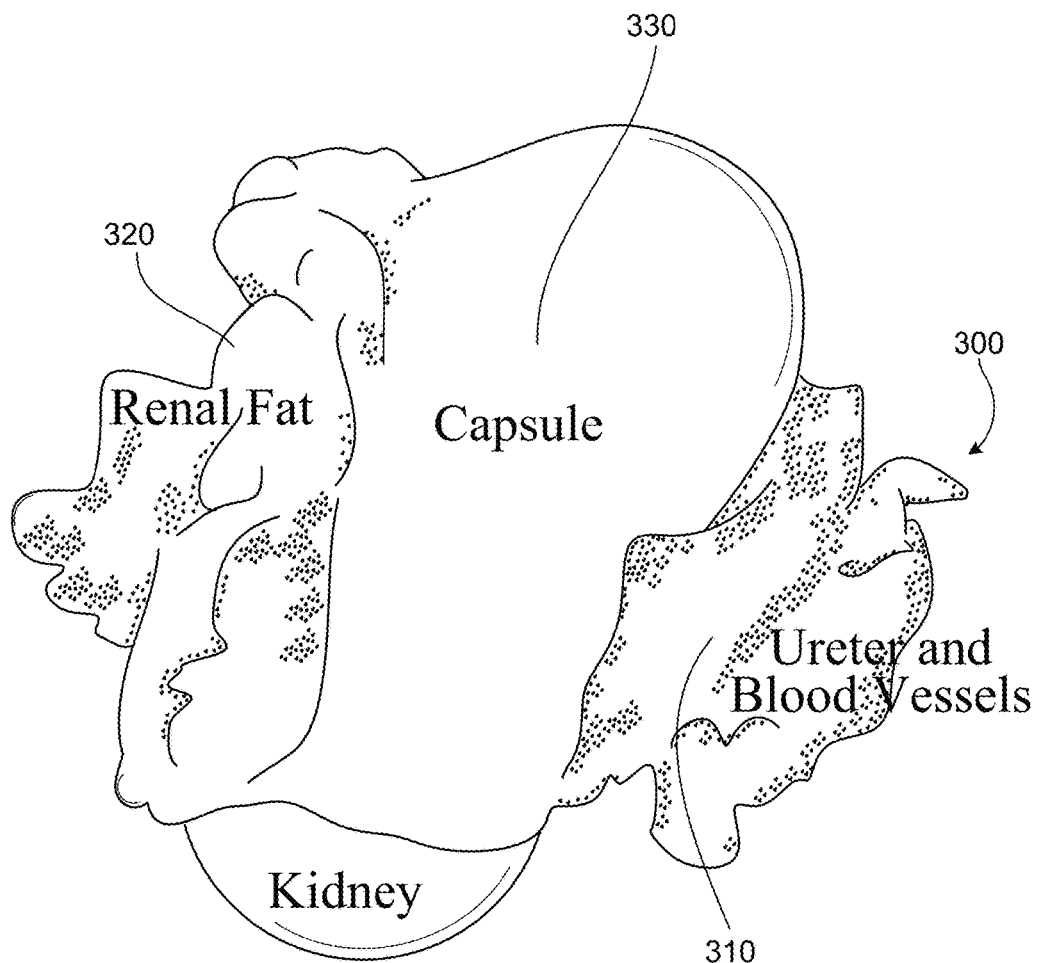
FIG. 3 depicts a porcine kidney.
Figure 4:
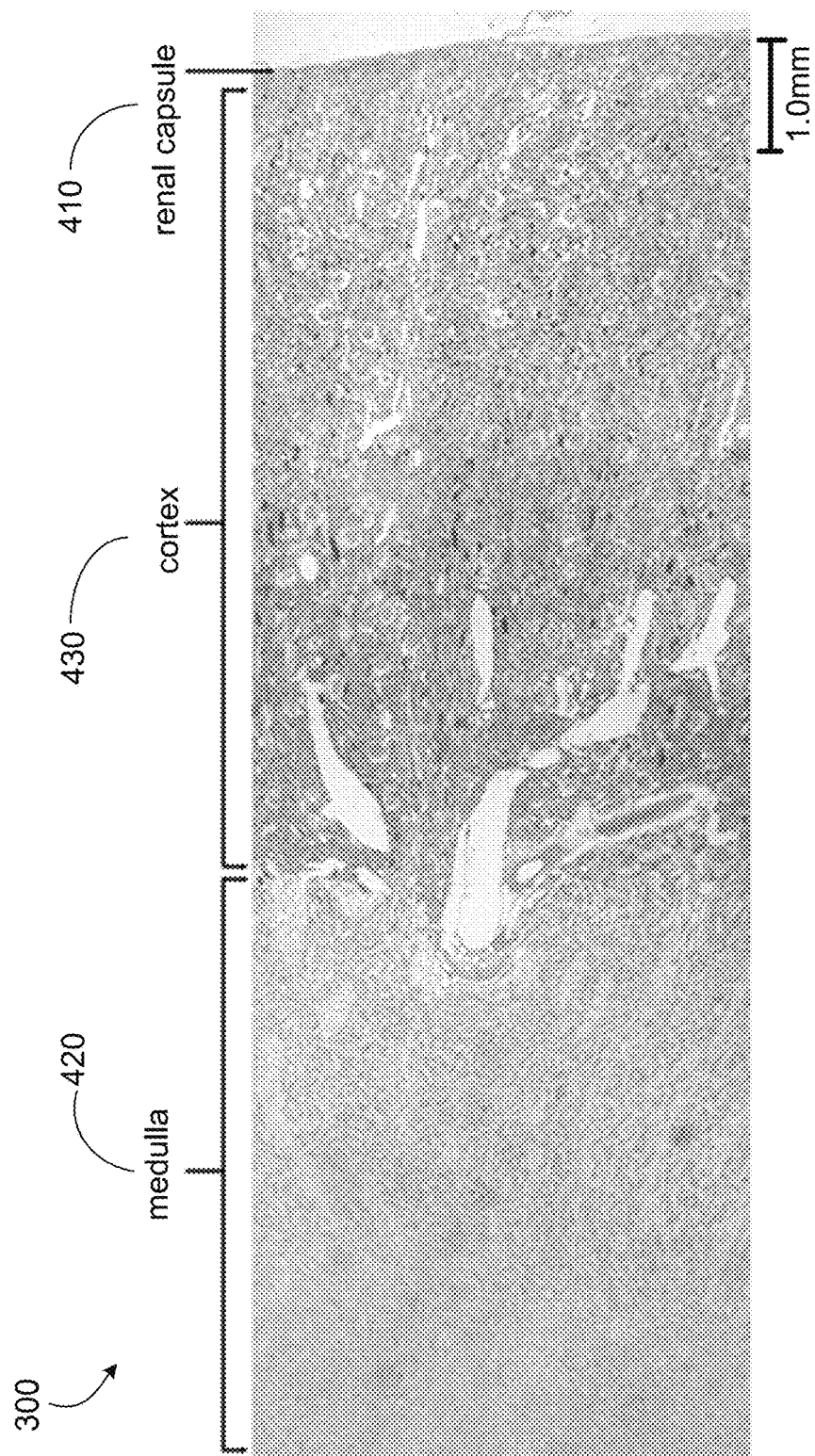
FIG. 4 depicts a cross-section of a kidney.

FIG. 1A is a flow chart depicting the overall process of incorporating kidney capsule tissue into a prosthetic heart valve. The first step, 11, is to procure a kidney capsule for use in a prosthetic heart valve. In some cases, a porcine kidney, such as depicted in FIG. 3, can be procured. In some cases, bovine, equine, sheep, or goat kidneys can be obtained. In some cases, the kidneys of other large farm animals can be used. Referring to FIG. 3, the kidney capsule 330 can easily be peeled away from kidney 300, and renal fat 320 and ureter and blood vessels 310 in nice larger sheets of tissue. In some cases, animal kidneys can be obtained from organizations that are certified by one or more government or non-government organizations as providing biological tissues suitable for use in medicines or medical devices and/or that the animals have been raised according to particular regulations, which can reduce the risk of transmitting agents of animal spongiform encephalopathies.

Figure 2:
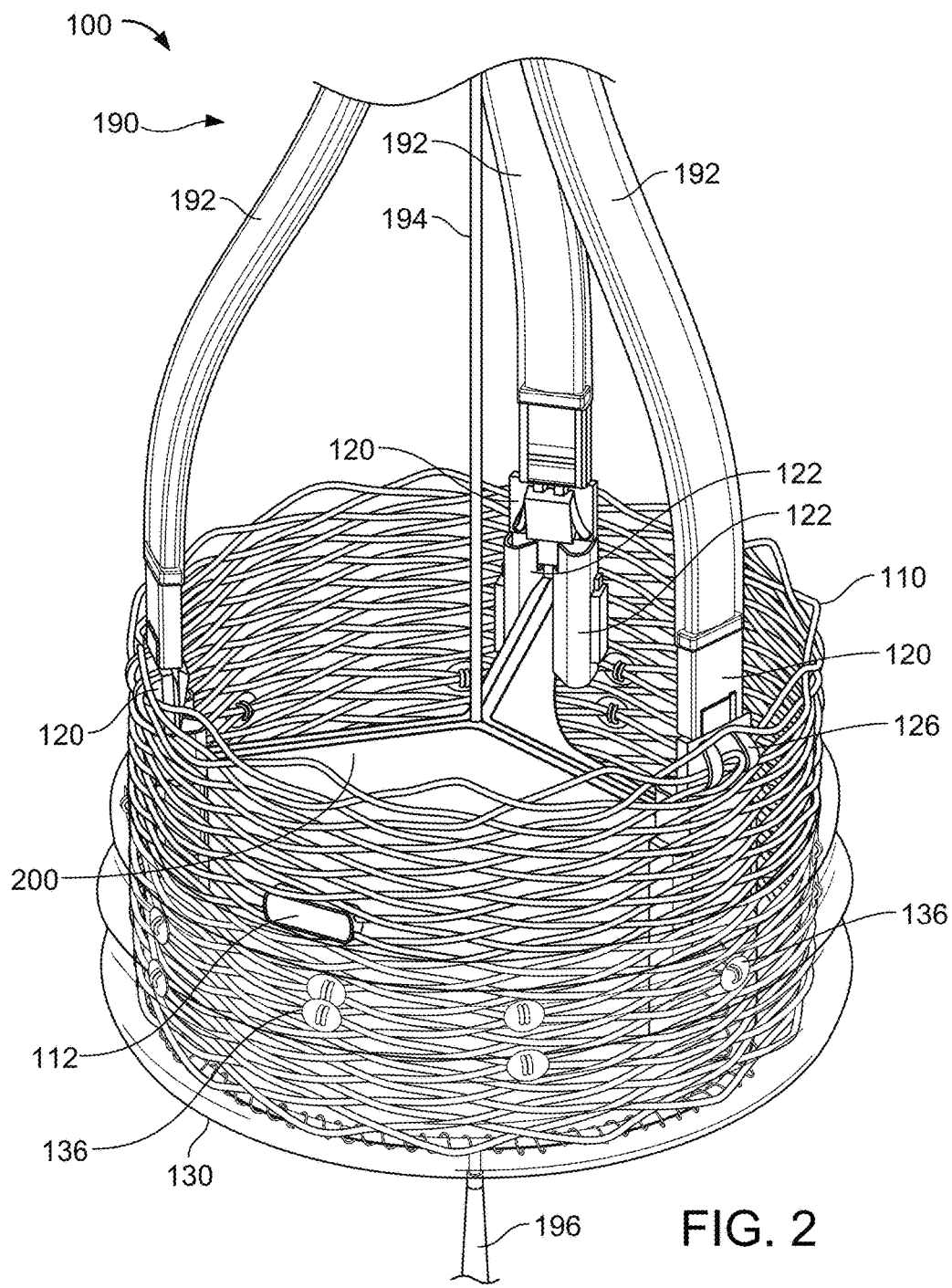
FIG. 2 is an exemplary prosthetic heart valve.

After obtaining a kidney and separating the kidney capsule, such as porcine kidney capsule 330, the kidney capsule can be bi-axially oriented and fixed in step 12, which is described below. In step 13, leaflets having a predetermined shape are cut from the fixed kidney capsule tissue, and suitable leaflets selected for use in a prosthetic heart valve, which is described below in connection to FIG. 5. In step 14, a prosthetic heart valve is fabricated using one or more of the cut leaflets. For example, FIG. 2 depicts an exemplary prosthetic heart valve. In some cases, three leaflets including the biaxially oriented and fixed kidney capsule tissue can be stitched to a frame and/or to each other to form a prosthetic heart valve. In step 15, prosthetic heart valves can be inspected and/or tested to ensure that they meet specifications. In some cases, a prosthetic heart valve can be sterilized before or after inspection.

Figure 1B:
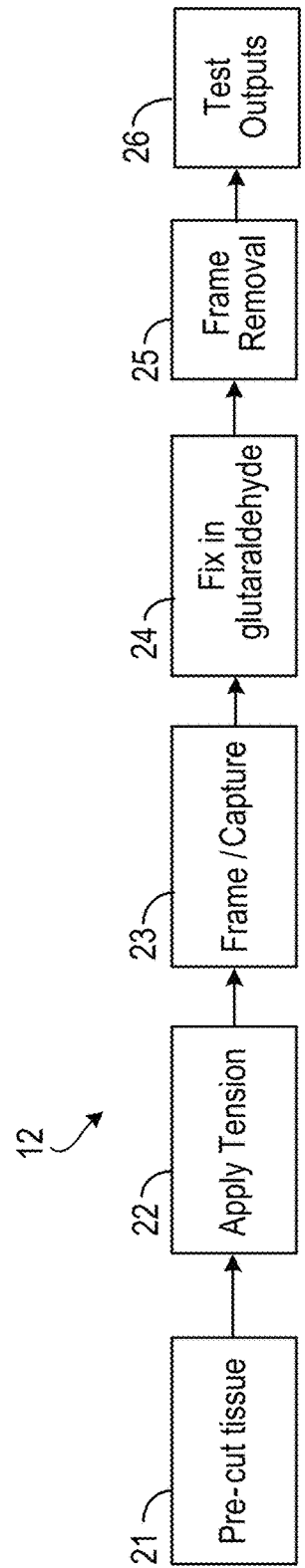
FIG. 1B is a flow chart depicting a method of treating kidney capsule tissue according to some embodiments of the methods provided herein.

Exemplary processes of fixing kidney capsule tissue 12 is further shown in the flow chart of FIG. 1B. Processes provided herein for kidney capsule tissue modification can use one or more of the steps depicted in FIG. 1B. In step 21, a patch of kidney capsule tissue is cut to simplify the tissue modification processes provided in steps 22-26. In some cases, the patch of kidney capsule tissue can be substantially rectangular. In some cases, the patch of kidney capsule tissue can be cut such that it can be laid in a substantially flat configuration. In some cases, the patch of kidney capsule tissue can be cut such that thickness variations are minimized. Step 21 can be performed by hand with the aid of a template approximating the shape of the biological tissue. In some cases, step 21 can be automated using opposite male and female mold members and a control system to cut the biological tissue along predetermined lines. Although the kidney capsule tissue can be cut in step 21 to minimize variations in mechanical properties of the kidney capsule tissue in the patch, natural variations are expected; thus the devices, systems, and methods provided herein can further tension and fix the kidney capsule tissue to produce reliable and consistent mechanical properties in the kidney capsule tissue. In some cases, the kidney capsule tissue can have an initial thickness of about 0.1 mm to about 3.0 mm.

Figure 5:
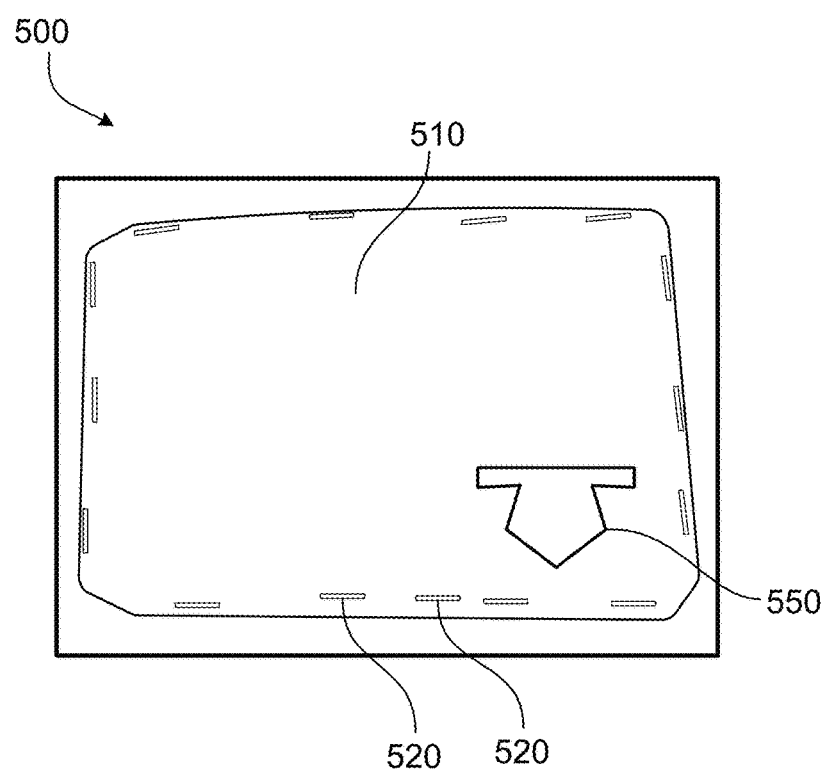
FIG. 5 depicts a frame for securing biaxially tensioned kidney capsule tissue for treatment and cutting of leaflets.

In step 22, the kidney capsule tissue is tensioned. For example, a plurality of grippers can be arranged around a patch of kidney capsule tissue placed over a frame and stretched to tension the patch of kidney capsule tissue. In step 23, the tensioned patch of kidney capsule tissue is captured on a frame, such as shown in FIG. 5, to retain the tensioning for further processing. For example, as shown in FIG. 5, tensioned patch 510 can be secured on the frame by a plurality of staple 520 to create a tissue-frame assembly 500. In step 24, the tensioned patch is chemically cross-linked to fix the biological tissue. As shown, step 24 can use a gluteraldehyde. In some cases, tissue-frame assembly 500 can be placed in a solution including 0.6 wt % gluteraldehyde for at least 10 minutes to chemically cross-link the kidney capsule tissue. In some cases, other chemical cross-linking agents can be used to chemically cross-link the kidney capsule tissue on the frame.

In step 25, oriented and fixed kidney capsule tissue can be separated from the frame. In some cases, the oriented and fixed kidney capsule tissue can be cut from the fixed and tensioned kidney capsule tissue while the fixed and tensioned kidney capsule tissue is still secured to the frame. In some cases, the fixed and tensioned kidney capsule tissue can be removed from the frame and subsequently cut. In step 26, the fixed and tensioned kidney capsule tissue is tested to determine if it meets specifications.

FIG. 2 illustrates an exemplary prosthetic heart valve 100 provided herein, which can use leaflets 200 including tensioned and fixed kidney capsule tissue provided herein. FIG. 2 is a perspective views of prosthetic heart valve 100 connected to a deployment device 190. As shown, prosthetic heart valve 100 includes an expandable member 110 (e.g., a braided stent), three bi-axially oriented and fixed kidney capsule leaflets 200, three anchor elements 120 that secure sleeve portions 216 of leaflets 200 to expandable member 110, and a tubular seal 130 secured around a blood inflow end of prosthetic heart valve 100. To facilitate better understanding, FIG. 2 does not show components that are located underneath tubular seal 130. Anchor elements 120 can include post leg compression elements 122 and clamping support structures 126 adapted to provide support along opposite sides of the sleeve portions 216. Expandable member 110 shown in FIG. 2 is a braided stent (which can also be described as a braided anchor element), which is adapted to transition between a restricted state having a smaller diameter and an expanded state having a larger diameter. Expandable member 110 can be self-expanding, mechanically expanded, or a combination thereof. In some cases, one or more radiopaque markers can be secured to prosthetic heart valves provided herein. As shown, expandable member 110 includes a radiopaque marker 112. Any suitable radiopaque material (such as platinum, palladium, gold, tantalum, or alloys thereof) can be used as the radiopaque material in radiopaque marker 112. One or more radiopaque markers can be used with an imaging system to help a physician ensure that a valve is set in an appropriate location. In some cases, prosthetic heart valves provided herein include at least three radiopaque markers. Expandable member 110 can have any suitable structure, arrangement, or material. In some cases, expandable member 110 can include a braided wire stent. For example, U.S. Publication Number 2005/0143809, titled, "Methods and Apparatus for Endovascularly Replacing a Heart Valve," and filed on Nov. 5, 2004, which is herein incorporated by reference for its disclosure of possible structures and materials for a braided wire stent, discloses a braided wire stent. In some cases, expandable member 110 includes a shape memory material (e.g., a nickel-titanium alloy or a cobalt-chromium alloy).

In some cases, as shown, prosthetic heart valve 100 includes three kidney capsule leaflets 200. In some cases, prosthetic heart valves provided herein can have any suitable number of kidney capsule leaflets, such as two, three, four, five, or more leaflets. In some cases, kidney capsule leaflets 200 are secured to one another. In some cases, kidney capsule leaflets 200 can be secured to one another by a suture (not shown) or a plurality of sutures. Kidney capsule leaflets 200 can be sutured alongside edges of a body portion of each leaflet. In some cases, prosthetic heart valves provided herein can include a single line of sutures, which can be adapted to minimize leaks, minimize the width of a seam, and/or minimize the profile of a replacement heart valve during a percutaneous insertion. In some cases, prosthetic heart valves provided herein can include multiple lines of sutures.

Referring back to FIG. 1B, step 22, a patch of kidney capsule tissue can be tensioned according to methods, devices, or systems provided herein. In some cases, a patch of biological tissue can be tensioned by securing the edges of the patch to a plurality of grippers and applying an equal amount of actuating force to each of the grippers. In some cases, a patch of biological tissue provided herein can be along a single axis for a uniaxial orientation. In some cases, a patch of biological tissue provided herein can be stretched along two axes for a biaxial orientation. In some cases, an amount of force supplied along the two intersecting axes is equal. In some cases, an amount of force supplied along the two intersecting axes is different. In some cases, the axes are perpendicular. In some cases, force is supplied along each axes such that each gripper supplies an equal amount of stretching force to the biological tissue.

A number of embodiments of the invention have been described. Nevertheless, it will be understood that various modifications may be made without departing from the spirit and scope of the invention. Accordingly, other embodiments are within the scope of the following claims.

What is claimed is:

1. A prosthetic heart valve comprising a plurality of leaflets secured together and retained within an expandable tubular member, each leaflet comprising kidney capsule tissue,
    wherein the kidney capsule tissue has been cross-linked while under a bi-axial tensioning to create a bi-axially oriented, cross-linked kidney capsule tissue that does not recoil when tension is released.

2. The prosthetic heart valve of claim 1, wherein each leaflet comprises multiple layers of kidney capsule tissue.

3. The prosthetic heart valve of claim 1, wherein the kidney capsule tissue is obtained from a farm animal.

4. The prosthetic heart valve of claim 1, wherein the kidney capsule tissue is bovine kidney capsule tissue.

5. The prosthetic heart valve of claim 1, wherein the kidney capsule tissue is porcine kidney capsule tissue.

6. The prosthetic heart valve of claim 1, wherein the kidney capsule tissue is equine kidney capsule tissue.

7. The prosthetic heart valve of claim 1, wherein the kidney capsule tissue is sheep kidney capsule tissue.

8. The prosthetic heart valve of claim 1, wherein the kidney capsule tissue is goat kidney capsule tissue.

9. The prosthetic heart valve of claim 1, wherein the kidney capsule tissue is chemically cross-linked with glutaraldehyde.

10. The prosthetic heart valve of claim 1, wherein the kidney capsule tissue has a thickness of between 25 microns and 75 microns.

11. The prosthetic heart valve of claim 10, wherein each leaflet has one or more layers of kidney capsule tissue to have a total thickness of between 50 microns and 0.33 mm.

12. The prosthetic heart valve of claim 1, wherein the kidney capsule tissue has a moisture content of between 73% and 94%.

13. The prosthetic heart valve of claim 1, wherein the kidney capsule tissue has an ultimate tensile strength of between 3.6 MPa and 8.0 MPa.

14. The prosthetic heart valve of claim 1, wherein the kidney capsule tissue has a thickness of about 43 microns, a moisture content of about 86% and an ultimate tensile strength of about 6.8 MPa.

* * * * *